(12) United States Patent
Kim et al.

(10) Patent No.: US 7,060,502 B2
(45) Date of Patent: Jun. 13, 2006

(54) METHOD OF DIAGNOSING THE CHANCES OF PREGNANCY AND THE DIAGNOSTIC KIT FOR THE SAME

(75) Inventors: Cheorl-Ho Kim, Bosung Mansion 201-407, Bummul-dong 1269, Susong-gu, Daegu 706-100 (KR); Dong-Mok Lee, Pohang-si (KR); Tae-Wook Chung, Busan (KR); Jeong-Heon Ko, Daejon (KR)

(73) Assignee: Cheorl-Ho Kim, Daegu (KR)

( * ) Notice: Subject to any disclaimer, the term of this patent is extended or adjusted under 35 U.S.C. 154(b) by 0 days.

(21) Appl. No.: 10/652,116

(22) Filed: Aug. 29, 2003

(65) Prior Publication Data

US 2004/0185575 A1 Sep. 23, 2004

(30) Foreign Application Priority Data

Mar. 20, 2003 (KR) .............................. 10-2003-0017447

(51) Int. Cl.
*G01N 33/48* (2006.01)
*G01N 33/53* (2006.01)

(52) U.S. Cl. ............................. 436/65; 436/510; 435/4; 435/23; 435/29

(58) Field of Classification Search .................... 436/65, 436/510; 422/61; 435/4, 23, 29, 810
See application file for complete search history.

(56) References Cited

U.S. PATENT DOCUMENTS 5,641,636 A * 6/1997 Strauss et al. ................ 435/7.4
5,698,404 A * 12/1997 Strauss et al. ................ 435/7.4
6,140,099 A * 10/2000 Strauss, III .................. 435/219

OTHER PUBLICATIONS

Product brochure for "EnzChek Gelatinase/Collagenase Assay Kit". Molecular Probes, Mar. 22, 2001, pp. 1–4.*
Bagavandos, 1998, J. Endocrinol. 158;221–228.
Sakkas et al., 2001, Fertil. Steril.76(6):1150–1156.
Riley et al., 1999, Mol. Hum. Reprod. 5: 376–381.
Huang et al., 1998, J. Clin. Endocrincol. Metab. 83: 1721–1729.
Hullboy et al., 1997, Mol. Hum. Reprod. 1: 27–45.
Alexander et al., 1996, Development 122: 1723–1736.
Leco et al., 1996, Mol. Reprod. Dev. 45: 458–465.
Jeziorska et al., 1996, J. Reprod. Fertil. 107: 43–51.
Draper et al., 1995, Am. J. Obstet. Gynecol. 173: 1506–1512.
Harvey et al., 1995, Development 121: 1005–1014.
Lefebvre et al., 1995, Development 121: 947–955.
Reponen et al., 1995, Develop. Dynam. 202: 388–396.
Lei et al., 1995, Biol. Reprod. 53: 339–344.
Luck et al., 1995, J. Endocrinol. 146: 191–195.
Vadillo–Ortega et al., 1995, Am. J. Pathol. 146: 148–156.
Bryant–Greenwood et al., 1995, Am. J. Obstet. Gynecol. 172: 63–70.
Cross et al., 1994, Science 226: 1508–1518.
Shimonovitz et al., 1994, Am. J. Obstet. Gynecol. 171: 832–838.
Rawdanowicz et al., 1994, J. Clin. Endocrin. Metab. 79: 530–536.
Espey, 1994, Biol. Reprod. 50: 233–238.
Sato et al., 1993, Oncogene 8: 395–405.
Behrendtsen et al., 1992, Development 114: 447–456.
Librach et al., 1991, J. Cell, Biol. 113: 437–449.
Murphy et al., 1991, Biochem. J. 277: 277–279.
Aplin et al., 1988, Cell. Tissue Res. 253: 2312–2340.
Wewer et al., 1986, Differentiation 32: 49–58.
Hibbs et al., 1985, J. Biol. Chem. 260: 2493–2500.
Fisher et al., 1985, J. Cell. Biochem. 27: 31–40.
Shalev et al. Molecular Human Reproduction, vol. 7, No. 4, pp. 325–331, 2001.*
Riley et al. Reproduction, vol. 121, pp. 553–560, 2001.*
Lahav–Baratz et al. Fertility and Sterility, vol. 79, No. 3, pp. 567–571, Mar. 2003.*

* cited by examiner

*Primary Examiner*—Maureen M. Wallenhorst
(74) *Attorney, Agent, or Firm*—Cheryl H. Agris

(57) ABSTRACT

Disclosed is a method of diagnosing the chances of pregnancy and the diagnostic kit for the method. In the present invention, follicular fluid is retrieved from the women who attended the in vitro fertilization program and matrix metalloproteinase activity is measured. According to the present invention, the chance of pregnancy in the group with low matrix metalloproteinase-9 activity is zero whereas in the group with high matrix metalloproteinase-9 activity, the chances are 50–60%. Therefore it is possible to predict the chances of pregnancy in assisted reproduction technology by measuring the degree of matrix metalloproteinase-9 expression by using the method and kit of the present invention enhancing the efficiency of assisted reproduction technology.

5 Claims, 3 Drawing Sheets

METHOD OF DIAGNOSING THE CHANCES OF PREGNANCY AND THE DIAGNOSTIC KIT FOR THE SAME

PRIORITY CLAIM

This application claims priority from Korean application no. 2003-17447, filed Mar. 20, 2003 under 35 U.S.C. 119 (a)–(d), the contents of which are incorporated herein by reference.

FIELD OF THE INVENTION

The present invention relates to a method of diagnosing the chances of pregnancy and the diagnostic kit for the method. More particularly, the invention relates to a method of diagnosing the chances of pregnancy by measuring MMP-9 activity contained in the follicular fluid.

BACKGROUND OF THE INVENTION

Since the first test-tube baby was born in 1979, various methods for assisted reproduction technology (ART) have been developed and applied to the treatment of sterile patients. Examples of ART are in vitro fertilization-embryo transfer (IVF-ET), intracytoplasmic sperm injection (ICSI), testicular sperm extraction (TESE), round spermatid injection (ROSI) and-embryo freezing. While ART is an important and general method for the treatment of sterile patients, there remain problems to be overcome, such as high costs, complicated procedure and low chance of success.

The use of ART is on the increase. The rate of pregnancy in IVF has increased but is not up to the expectation. The actual take home baby rate is 15–30%. According to the U.S. statistics, the pregnancy rate and delivery rate per cycle by using IVF in 1996 was 23.8% and 19.3% respectively. In 1997 statistics, these rates increased to 29.3% and 24.0% each. However, there was no substantial difference between 1996 statistics and 1997 statistics.

The successful human pregnancy is dependent upon follicular development, number of oocytes retrieved, fertilization, embryo development and implantation, during an assisted reproductive technology (ART) cycle (Sakkas D, et al., 2001). Among them, blastocyst implantation into the human uterus is a complex process dependent on profound structural changes in the endometrium and the developing embryo. Tissue remodeling is requisite to uterine preparation, embryonic breaching of the epithelial basement membrane and subsequent penetration of the endometrial stroma.

It is thought that matrix metalloproteinases (MMPs) are essential for the breakdown of extracellular matrix (ECM) components during this process. MMPs are an important family of zinc-dependent enzymes with a broad range of substrate specificities capable of the breakdown of extracellular matrix (Hulboy et al., 1997). Many studies suggest that the MMPs play an important role in tissue remodeling and tissue repair under various physiological and pathological conditions such as morphogenesis, ovulation, angiogenesis, arthritis, wound healing and tumor invasion. (Behrendtsen et al., 1992; Cross et al., 1994; Lefebvre et al., 1995; Harvey et al., 1995; Leco et al., 1996; Alexander et al., 1996) However, little is known about the physiological regulation of MMPs and the mechanism whereby these proteases are activated in vivo.

Collagenolytic enzymes, particularly MMPs, are thought to play a vital role in ovulation in other species. Examples include the fibrillar collagenases such as MMP-1, which break down the fibrillar collagen forms that confer much of the structural integrity to the ovarian stroma. Expression of MMP-9, also known as 92 kDa type IV collagenase/gelatinase B, has also been detected in mouse and human pre-implantation embryos, EC cells, and blastocyst outgrowths by zymography, immunocytochemistry, and PCR. Culture of blastocyst outgrowths in the presence of fibroblast growth factor-4 increased secretion of MMP-9. MMP-9 has been shown to be developmentally regulated in mouse blastocysts and cytotrophoblast cells during embryo implantation. On the other hand, successful pregnancy is dependent upon invasion of trophoblast into the decidua at implantation, and subsequently the further invasion of extravillous trophoblast into the walls of the maternal spiral arterioles (Fisher et al., 1985; Librach et al., 1991; Cross et al., 1994). These events require the breakdown of extracellular matrix and cellular migration. In rat and human fetal membranes, the amount of MMP-9 is increased with labour (Bryant-Greenwood and Yamamoto, 1995; Draper et al., 1995; Lei et al., 1995).

Among MMPs, the MMP-9, degrades a variety of extracellular matrix components including many kinds of collagens (IV, V and XI), elastin, proteoglycan and gelatin (Hibbs et al., 1985: Murphy et al., 1991). Moreover, previous studies have demonstrated that the secretion of MMP-9 from human cervical fibroblasts (Sato, H. and Seiki, M., 1993), trophoblasts (Shimonovitz, S. et al., 1996) and endometrial stromal cells (Huang, H. A., et al., 1998) is stimulated by cytokines and hormones. MMP-9 has been suggested to intervene at different stages of the cyclical changes in female reproduction (Jeziorska, M., et al., 1996; Librach, C. L. et al. 1991; Vadillo-Ortega, F. et al., 1995), such as in the menstrual cycle, ovulation, implantation, parturition, and involution of the mammary glands after lactation. Ovulation is a process triggered by the preovulatory surge of LH from the pituitary gland, which results in the liberation of the mature ovum from the preovulatory ovarian follicle. Additionally, ovulation is probably a result of controlled enzymatic degradation and loss of collagen in the follicle wall (Espey, 1994; Luck and Zhao, 1995). Although this process requires extensive tissue remodeling, and MMP-9 is important for generating the proteolytic activity needed at the time of ovulation, little is known about the relationship between MMP-9 and follicular fluid of human. The presence of MMP-9 in follicular fluid, which have substrate specificities that include the basement membrane constituent collagen IV, indicates that they are likely to be required for tissue remodeling during follicle growth and development.

SUMMARY OF THE INVENTION

The object of the present invention is to provide a method of diagnosing the chances of pregnancy and the diagnostic kit for the method of assisted reproduction technology such as in vitro fertilization.

To accomplish this object, follicular fluid is retrieved from the women who attended the in vitro fertilization program and MMP activity is measured. It is shown that the chance of pregnancy in the group with low MMP-9 activity is zero whereas in the group with high MMP-9 activity, the chances are 50–60%. Therefore it is possible to predict the chances of pregnancy in ART by measuring the degree of MMP-9 expression by using the method and kit of the present invention, thus enhancing the efficiency of ART. The inventors of the present invention examined whether the expression of MMP-9 from follicular fluid is related to pregnancy during in vitro fertilization cycle. The results of the present invention show higher expression of MMP-9 in the follicular fluid is associated with higher implantation and pregnancy rate.

Therefore, the invention is directed to a method for predicting pregnancy outcome in a human female subject comprising
(a) measuring the activity of MMP-9 in the follicular fluid from a follicle of a mature oocyte and
(b) predicting from the activity of MMP-9 measured the probability of establishing pregnancy.

Furthermore, the invention is directed to a method for predicting whether implantation of a fertilized oocyte from a human female subject will result in pregnancy in a female subject following in assisted reproductive technology (ART), e.g., in vitro fertilization-embryo transfer, comprising
(a) removing oocytes together with follicular fluid from a female subject;
(b) measuring the activity of MMP-9 in the follicular fluid;
(c) predicting from the activity of MMP-9 measured the probability of establishing pregnancy by in vitro fertilization-embryo transfer and
(d) fertilizing oocytes from a human female subject whose MMP-9 activity is above a predetermined threshold level.

The invention is also directed to a diagnostic kit for predicting pregnancy outcome comprising a protein substrate from MMP-9.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise. The terminology used herein is for the purpose of describing particular embodiments only, and is not intended to be limiting, since the scope of the present invention will be limited only by the appended claims.

BRIEF DESCRIPTION OF THE DRAWINGS

FIG. 1A shows Zymography of MMP-9 activity and FIG. 1B shows Zymography of MMP-2 activity. Lane C represents MMP-9 control, lanes 1–5 represent pregnancy, and lanes 6–10 represent nonpregnancy. In this analysis, samples were electrophoresed on 0.1% gelatin/7.5% SDS-PAGE gel, washed and allowed to digest the gelatin overnight in zymography incubation buffer.

DETAILED DESCRIPTION OF THE INVENTION

Figure 1:
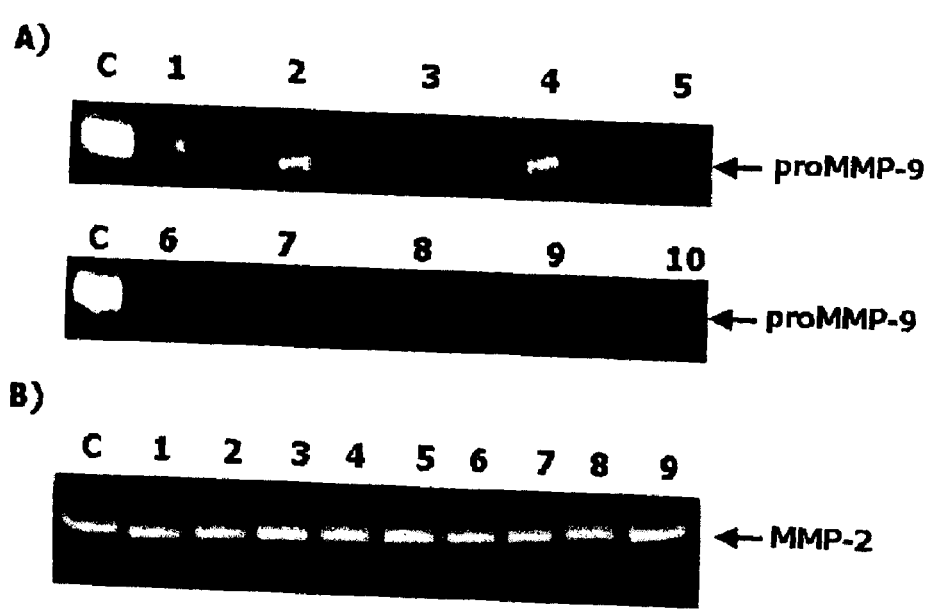
FIG. 1 shows zymography analysis of MMP-9 and MMP-2 activities in the follicular fluid of a human female patient.

One aspect of the present invention is to provide a method of diagnosing the chances of pregnancy by measuring the activity of MMP-9 contained in the follicular fluid of a follicle having a mature oocyte.

One detailed feature of the present invention is that in the method of diagnosing the chances of pregnancy, the activity of MMP-9 is measured by using zymography.

Another detailed feature of the present invention is that in the method of diagnosing the chances of pregnancy, the diameter of the follicles selected is not less than 17 mm.

Another aspect of the present invention is to provide a diagnostic kit of diagnosing the chances of pregnancy, which measures the activity of MMP-9 contained in the follicular fluid by using polyacrylamide gel containing protein substrate which is decomposed by MMP-9.

Another detailed feature of the present invention is that in the diagnostic kit of diagnosing the chances of pregnancy, the protein substrate is selected from the group consisting of collagen IV, collagen V, collagen VI, elastin, proteoglycan and gelatin.

The changing endocrine state of the female during the reproductive cycle and pregnancy results in extensive tissue remodeling in the uterus (Wewer et al., 1986; Aplin et al., 1988). For example, the various basement membrane components, such as type IV collagen, laminin, fibronectin, and proteoglycans in the human uterus undergo changes throughout the menstrual cycle and pregnancy (Aplin et al., 1988). Likewise, mouse uterine stromal cells undergoing decidualization also remodel the extracellular matrix components (Wewer et al., 1986), and MMPs and TIMPs (tissue inhibitor of matrix metalloproteinase) are thought to be key mediators for degradation of matrix during ovulation, implantation and decidualization (Behrendtsen et al., 1992; Cross et al., 1994; Lefebvre et al., 1995; Harvey et al., 1995; Leco et al., 1996; Alexander et al., 1996).

As will be described in the Example below, the activity of MMP-9 in human follicular fluid at superovulation has been demonstrated by gelatin substrate zymography and the MMP-9 activity was increased significantly ($P<0.01$) in the pregnant group compared to the non-pregnant group. However, MMP-2 activities were observed with high amounts in follicular fluid of all the tested woman without any difference between pregnant and non-pregnant group. When the MMP-9 activities of the follicular fluids were visualized and normalized to densitometric units, the mean MMP-9 densitometry for pregnancy group was 61,759 units. These results clearly suggested that MMP-9 activity is stringent factor for successful pregnancy.

By using the method of the present invention, the problem of the low chances of actual delivery in ART can be solved, and the possibility of pregnancy can be predicted at early stage. Also, by sorting out the group with no expression of MMP-9, new treatment can be applied before ART in order to raise the chances of pregnancy.

EXAMPLE

The present invention will be described by the Example, infra. The example is for the illustrative purpose only and is not intended to limit the invention to the specific form.

Materials and Methods

Patients Characteristics 54 patients who underwent IVF-ET program of the women's Human Infertility of Dongguk Unviersity for a variety of infertility problem were included in this study. Causes of infertility were included tubal factors (n=15), endometriosis (n=11), anovulation (n=9) and unexplained infertility (n=19). The female partners were between 21 and 33 years old (average, 31.3 years old). Couples with male factor infertility such as sperm deficiency were excluded from this study.

Process of ART

1. Preparation of Oocyte

Ovarian induction was performed by gonadotropin-releasing hormone agonist (GnRH-a). 900 buserelin (Hoechst, Germany) is sprayed to the nasal cavity for pituitary desensitization during luteal phase and human menopausal gonadotropin (hMG, Pergonal, Serono or IVF-M, LG, Korea) is injected 3–5 days after the start of follicular phase. The amount of hMG is adjusted according to the response of follicle using negative vaginal ultrasound scan. Ovulation was induced with 10,000 IU of human chorionic gonadortopin (hCG, IVF-C, LG, Korea) when the patients had more or two follicles greater than 17 mm in diameter. Oocyte retrieval was performed 36 hours after the injection of hCG by aspiring follicle using vaginal ultrasound. The oocyte retrieved was placed in the manipulator (IVF chamber, USA) with 37° C. temperature and 5% $CO_2$ and the maturity of the oocyte is measured by observing the properties of ovarian cell and the existence of GV in the cytoplasm using dissecting microscope (SMZ-10, Nicon, Japan). Then the oocyte was transferred to culture plate (3037, Falcon, USA) which contained P1 media added with 10% SSS (serum substitute supplement; Irvine Science, Santa Ana, Calif., USA) and cultured in the $CO_2$ cultivator. The number of oocytes used is not more than 5 per culture plate.

2. External Fertilization

After retrieving oocytes, sperm is collected to the specimen container (Baxter, USA) through masturbation. The concentration and mobility of sperms are measured according to the standard of WHO. The sperm is maintained in the room temperature environment for 10 to 20 minutes to obtain liquid phase sperm. The liquid phase sperm is transferred to 15 ml conical tube (2099, Falcon, USA) and centrifuged using Ham's F-10 containing 10% SSS at 1500 rpm twice for 5 and 3 minutes each. Supernatant liquid of centrifuged sperm is removed and Ham's F-10 containing 10% SSS is cautiously added to the remaining pellet so that the sperm can float. Floating sperm is stored in the 5 ml tube (2003, Falcon, USA) and used for fertilization. $1 \times 10^5$/ml of sperms are injected to the cultured oocyte. In the following morning, the oocyte retrieved was transferred to the manipulator with 37° C. temperature and 5% $CO_2$ and ovarian cell is removed by using syringe needle (320310, BD, USA) while observing with dissection microscope to determine the success of fertilization. Female pronucleus and male pronucleus are observed to be formed and two polycytes existed and from this observation the success of fertilization could be confirmed.

3. Transfer of Embryo

The embryos which had been successfully fertilized were collected and cultured in the P1 media for 48 hours, and 2–5 embryos with 8th cell period were selected and transferred into the uterine cavity. In most cases, a Tomcat catheter (8890-793021, Sherwoo, USA) is used for transfer.

4. Injection of Luteal Hormone and Confirmation of Fertilization

Everyday 100 mg of luteal hormone (progesterone in oil, Progest, Samil, Korea) is injected to the patients by intramuscular injection. 10 days after the transfer, biochemical pregnancies were defined as those pregnancies with a transient elevation of serum β-hCG level (>10 mIU/ml). A clinical pregnancy was defined as the presence of at least one gestational sac with fetal cardiac activity detectable by vaginal ultrasound.

Preparation of Follicular Fluid

Follicular fluid was obtained from follicle with diameter of not less than 17 mm which is retrieved by ultrasound-guided aspiration from women whose cycles were stimulated and who attended the IVF program. Oocyte retrieval and follicular fluid collection were carried out by ultrasound-guided aspiration and only follicular fluid containing very little blood is used. Follicular fluid was centrifuged at 3500 rpm for 30 minutes to remove blood and granulosa cells. The supernatant is sterilized by 0.2 μm of sterilizing filter and stored in the refrigerator with temperature −20° C. Later the fluid is melted for use.

Measuring MMP-9 Activity Using Zymography

Expression of gelatinases (MMP-2 and MMP-9) in follicular fluid was detected using zymography as described by Rawdanowicz et al. (1994) with minor modifications (Riley et al., 1999). Follicular fluid samples were separated by SDS-PAGE (7.5% (w/v gels; Minigel apparatus; Bio-Rad, Hemel Hempsead) using gels containing gelatin (1 mg/ml) in non-reducing conditions. Gels were washed in 2.5%(v/v) Triton X-100 and incubated in digestion buffer (200 mM NaCl, 50 mM Tris-HCl, 2.5 mM $CaCl_2$, 1 μM $ZnCl_2$, pH 7.6; all chemicals from Sigma Chemical Co, St Louis, Mo.) for 18 hr at 37° C. The gels were stained in staining solution (0.5% (w/v) Coomassie blue R250 (Bio Rad, Richmond, Calif.) in 30%(v/v) methanol 10% (v/v) glacial acetic acid in $H_2O$) at room temperature.

Quantification of MMP-9 Activity

Gelatinase activities were quantified using Gel Documentation semi-automated image analysis (Core-Bio System, Seoul, Korea) which quantified both the surface and the intensity of the lysis bands after scanning of the gels.

Statistical Analysis

Results are presented as the average±SE of at least three separate experiments. Statistical differences were evaluated by analysis with Student's t-test. Values of $P<0.05$ were accepted as significant.

Results

In follicular fluid, the gelatinase activity was present at 92 kDa, corresponding to the latent from of MMP-9, as demonstrated by zymography (FIG. 1). The abundance of MMP-9 increased significantly ($P<0.01$) in pregnant group when compared with the non-pregnant group.

Figure 2:
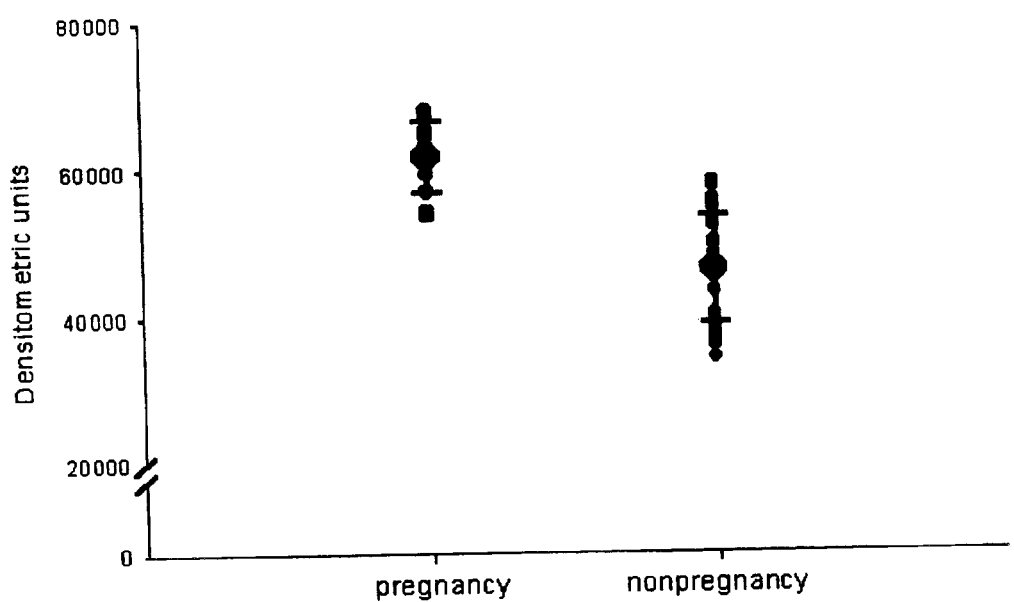
FIG. 2 shows the relation between the expression of MMP-9 and pregnancy rate in follicular fluid IVF.

Gelatinase activity was also detected at 72 kDa, corresponding to latent MMP-2 with high amounts secreted into follicular fluid of all women. However, no significant differences in MMP-2 expressions were found between pregnant and non-pregnant group. (FIG. 2).

The mean (±SD) age of women undergoing treatment was 31 years (±3.3). After one treatment cycle, oocytes were successfully retrieved in all cases (n=54). Oocyte retrieval was accomplished 36–37 hours after i.m. administration of hCG. The mean (±SD) fertilization rate for pregnant was 71.82% (11.7), whereas it was 69.1%(13.1) in not pregnant. Therefore, all women had a transfer of two to seven embryos. There were 16 clinical pregnancies noted: 1 missed abortions and 15 ongoing or delivered pregnancies. No age difference existed between women who conceived and those who did not; mean (±SD) age was 29(±3.3) and 31(±2.3), respectively (Table 1).

TABLE 1

Patient characteristics and MMP-9 expression in follicular fluid according to pregnant parameter

| Variable | Pregnant (n = 16) | Non-pregnant (n = 38) |
|---|---|---|
| No. of cycles | 16 | 38 |
| Age (years) | 29 ± 3.3 | 31 ± 2.3 |
| No. oocytes/patient | 13.4 ± 1.2 | 13.5 ± 1.4 |
| % Fertilization | 65.9 ± 17.3 | 67.3 ± 17.2 |
| No. embryo transfer | 4.7 ± 0.9 | 4.7 ± 0.6 |
| Duration of infertility (years) | 2.2 ± 0.9 | 1.9 ± 0.6 |
| Mean (±SD) MMP-9 activity (densitometry) | 61,759 ± 4800 | 47,021 ± 7981 |

All values are means ± SD

Figure 3:
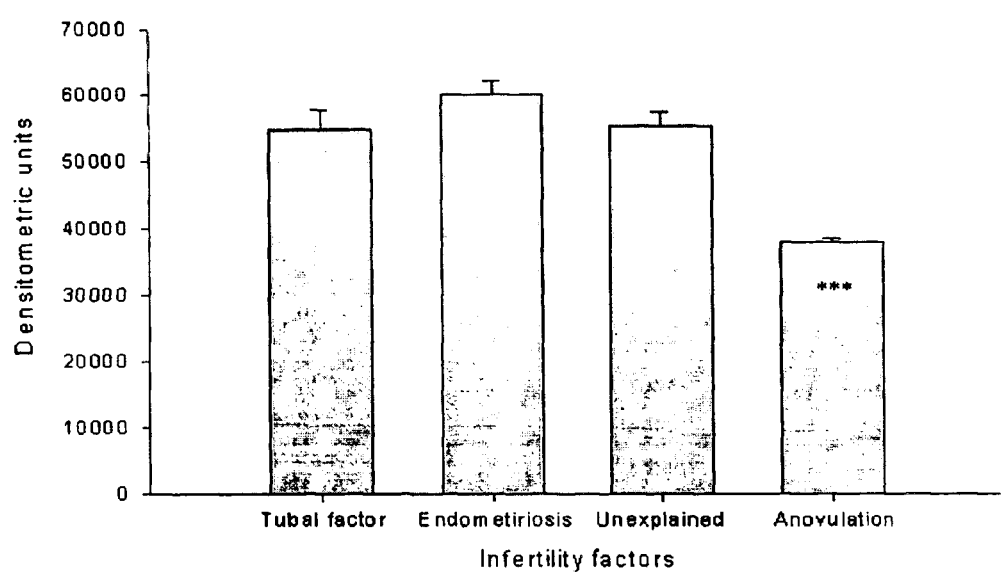
FIG. 3 shows the relation between the expression of MMP-9 in follicular fluid and infertility factors of the patients involved in the study.

When MMP-9 activities of the follicular fluids were visualized using zymographic method and normalized to densitometric units, the mean MMP-9 densitometry for pregnancy was 61,759 units. A total of 54 women were included in the study. Mean densitometry of MMP-9 expression in the tubal factor (n=15), endometriosis (n=11), unexplained (n=19) and anovulation (n=9) groups are shown in FIG. 3. The densitometry of the anovulation group was significantly lower than those of the other three groups (P<0.001).

Total of implantation and pregnancy rates were 18.6% and 29.6%, respectively. Table 2 show the pregnancy rate (PR) and implantation rate (IR) according to four arbitrary groups of MMP-9 expression values as follows: group 1, MMP-9 densitometric 30,000–40,000 units; group 2, 40,000–50,000 units; group 3, 50,000–60,000 units and group 4, MMP-9>60,000 units.

Interestingly, when the MMP-9 expression levels were less than 50,000 units using the densitometry, the implantation and pregnancy rates were all 0%. In contrast, when the levels of MMP-9 expression were greater than 50000 units, the implantation and pregnancy rates were 32.1% and 47.3% respectively. (Table 2).

TABLE 2

Implantation and pregnancy rates according to MMP-9 expression ranges in follicular 5fluid of human

| | MMP-9 densitometric unit (×10³) | | | |
|---|---|---|---|---|
| Variable | 30–40 | 40–50 | 50–60 | 60–70 |
| Implantation rate (%) | 0/49(0) | 0/62(0) | 28/87(32.1) | 21/65(32.3) |
| Pregnancy rate (%) | 0/10(0) | 0/10(0) | 9/19(47.3) | 7/15(46.6) |

This study demonstrates that deficiency of MMP-9 expression in follicular fluid resulted in non-pregnancy. Thus, it has been suggested that MMP-9 expression is essential in implantation and pregnancy and this expression is closely related with MMP-9 expression during ovulation. In conclusion, MMP-9 is likely to play a role in breakdown in extracellular matrix during follicle growth and development, in follicle migration and in ovulation and in controlling other cell functions, including the cell cycle.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

REFERENCES

1. Sakkas D, Percival G, D'Arcy Y, Sharif K, Afnan M. Assessment of early cleaving in vitro fertilized human embryos at the 2-cell stage before transfer improves embryo selection. Fertil Steril 2001. 76(6):1150–1156.
2. Hibbs M S, Hasty, K A, Seyer J M, Kang A H, Mainardi C L (1985)Biochemical and immunological characterization of the secreted forms of human neutrophil gelatinase. J. Biol. Chem. 260:2493–2500.
3. Murphy G, Cockett M I, Ward R V and Docherty A J. Matrix metalloproteinase degradation of elastin, type IV collagen and proteoglycan. A quantitative comparison of the activities of 95 kDa and 72 kDa gelatinases, stromelysins-1 and -2 and punctuated metalloproteinase (PUMP). Biochem J. 1991. 277: 277–279.
4. Sato H, Seiki M(1993) Regulatory mechanism of 92 kDa type IV collagenase gene expression which associated with invasiveness of tumor cells. Oncogene 8:395–405.
5. Shimonovitz S, Hurwitz A, Dushnik M, Anteby E, Geva-Eidar T, Yagel S. Developmental regulation of the expression of 72 and 92 kd type IV collagenases in human trophoblasts: A possible mechanism for control of trophoblast invasion. Am J Obstet Gynecol 1994: 171:832–838.
6. Huang H Y, Wen Y, Irwin J C, Kruessel J S, Soong Y K, Polan M L. Cytokine-mediated regulation of 92-kilodalton type IV collagenase, tissue inhibitor of metalloproteinase-1(TIMP-1) and TIMP-3 messenger ribonucleic acid expression in human endometrial stromal cells. J. Clin. Endocrinol. Metab. 1998:83:1721–1729.
7. Jeziorska, M. Nagase H. Salamonsen, L. A and Wolley. D. E (1996) Immunolocalization of the matrix metalloproteinases gelatinase B and stromelysin 1 in human endometrium throughout the menstrual cycle. J. Repro. Fertil. 107, 43–51.
8. Librach C L, Werb Z, Fitzgerald M L, Chiu K, Corwin N M, Esteves R A, Grobelny D, Galardy R, Damsky C H and Fisher S J(1991)92 kDa type IV collagenase mediates invasion of human cytotrophoblasts Jounal of Cell Biology113 437–449.
9. Vadillo-Ortega, F. Gonzalez-Azila, G, Furth, E. E. et al. (1995)92-kd type IV collagenase (matrix metalloproteinase-9) activity in human amniochorin increases with labor. Am.J.Pathol.146, 148–156.
10. Wewer U M, Damjanov A, Weiss J, Liotta L A, Damjanov I (1986): Mouse endometrial stromal cells produce basement-membrane components. Differentiation 32: 49–58.
11. Aplin J D, Charlton, A. K., Ayad, S.(1988): An immunohistochemical study of human endometrial extracellular matrix during the menstrual cycle and first trimester of pregnancy. Cell Tissue Res 253: 2312–40.
12. Behrendtsen O, Alexander C M, Werb Z (1992): Metalloproteinases mediate extracellular matrix degradation by cells from mouse blastocyst outgrowths. Development 114: 447–456.
13. Cross J C, Werb Z, Fisher S J (1994): Implantation and the placenta: Key pieces of the development puzzle. Science 226: 1508–1518
14. Lefebvre O, Regnier C , Chenard M-P, Wendling C, Chambon P, Bassett P, Rio M. C. (1995): Developmental expression of mouse stromelysin-3 mRNA. Development 121: 947–955.

15. Harvey M B, Leco Kj, Arcellana-Panlilio M Y, Zhang X, Edwards D R, Schultz G A (1995) Proteinase expression in early mouse embryos is regulated by leukaemia inhibitory factor and epidermal growth factor. Development 121: 1005–1014.
16. Leco K J, Edwards D R, Schultz G A (1996): Tissue inhibitor of metalloproteinases-3 is the major metalloproteinases inhibitor in the decidualizing murine uterus. Mol. Reprod. Dev. 45: 458–465.
17. Alexander C M, Hansell E J, Behrendtsen O, Flannery M L, Kishnani N S, Hawkes S P, Werb Z (1996) Expression and function of matrix metalloproteinases and their inhibitors at the maternal embryonic boundary during mouse embryo implantation. Development 122: 1723–1736.
18. Espey L L(1994) Current status of the hypothesis that mammalian ovulation is comparable to an inflammatory reaction. Biol. Reprod. 50: 233–238.
19. Luck M R and Zhao Y (1995) Structural remodelling of reproductive tissues. J. Endocrinol. 146, 191–195.
20. Reponen P, Leivo I, Sahberg C, Apte S S, Olsen B R, Thesleff I, Tryggvason K. 92-kDa type IV collagenase and TIMP-3 but not 72 kDa type IV collagenase or TIMP-1 or TIMP-2, are highly expressed during mouse embryo implantation. Develop Dynam 1995; 202:388–396.
21. Fisher S J, Leitch M S, Kantor M S (1985) Degradation of extracellular matrix by the trophoblastic cells of first trimester human placentas. J. Cell Biochem 27: 31–40.
22. Librach C L, Werb Z I, Fitzgerald M L, Corwin N M, Esteves R A, Grobelny D, Galardy R, Damsky C H and Fisher S J 92 kDa type IV collagenase mediates invasion of human cytotrophoblasts. J.Cell Biol 1991; 113: 437–449
23. Hulboy D L, Rudolph L A, Matrisian L M. Matrix metalloproteinases as mediators of reproductive function. Mol Hum Reprod 1997 January 3(1); 27–45
24. Bryant-Greenwood G D and Yamamoto S Y (1995): Control of peripartal collagenolysis in the human choriodecidua. Am. J. Obstet. Gynecol., 172: 63–70.
25. Draper D, McGregor J, Hall J (1995) Elevated protease activities in human amnion and chorion correlate with preterm premature rupture of membrane. Am. J. Obstet. Gynecol. 173: 1506–1512.
26. Lei H, Vadillo-Ortega F, Paavola L G and Strauss J F (1995) 92 kDa gelatinase (matrix metalloproteinase-9) is induced in rat armion immediately prior to parturition. Biol. Reprod. 53: 339–344.
27. Riley et al., 1999, Mol. Hum. Reprod. 5:376
28. Rawdanowicz et al., 1994, J. Clin. Endocrin. Metab. 79:530–536.

What is claimed is:

1. A method for predicting whether implantation of a fertilized oocyte from a human female subject will result in pregnancy in a female subject following assisted reproductive technology comprising (a) removing oocytes together with follicular fluid from a female subject;
   (b) measuring the activity of matrix metalloproteinase-9 in the follicular fluid;
   (c) predicting from the activity of matrix metalloproteinase-9 measured the probability of establishing pregnancy by in vitro fertilization-embryo based upon a predetermined threshold level of the matrix metalloproteinase-9 transfer and
   (c) fertilizing oocytes from a human female subject whose matrix metalloproteinase-9 activity is above the predetermined threshold level.

2. The method according to claim 1, wherein the activity of matrix metalloproteinase-9 is measured by using zymography.

3. The method according to claim 1, wherein the follicular fluid is collected from a follicle having a diameter not less than 17 mm.

4. The method according to claim 1, which further comprises obtaining said follicular fluid from a follicle of a mature oocyte.

5. The method according to claim 1, wherein the activity of matrix metalloproteinase 9 is measured by a matrix metalloproteinase-9 diagnostic kit comprising a protein substrate for matrix metalloproteinase-9, wherein said protein substrate is selected from the group consisting of collagen IV, collagen V, collagen VI, elastin, proteoglycan, and gelatin.

* * * * *